United States Patent [19]

Woolard

[11] Patent Number: 4,855,478

[45] Date of Patent: Aug. 8, 1989

[54] N,N'-DIARYL-N-ALKYLUREAS AND METHOD OF USE

[75] Inventor: Frank X. Woolard, Berkeley, Calif.

[73] Assignee: ICI Americas Inc., Wilmington, Del.

[21] Appl. No.: 128,005

[22] Filed: Nov. 30, 1987

[51] Int. Cl.$^4$ .................. C07C 127/01; C07C 157/02
[52] U.S. Cl. ........................... 558/417; 564/26; 564/29; 564/53; 564/54; 564/48
[58] Field of Search ............... 558/417; 564/26, 29, 564/48, 53, 54

[56] References Cited

U.S. PATENT DOCUMENTS

| | | | |
|---|---|---|---|
| 3,200,035 | 8/1965 | Martin | 564/54 |
| 3,903,130 | 9/1975 | Teach | 558/417 X |
| 4,111,683 | 9/1978 | Singer | 564/53 X |
| 4,127,673 | 11/1978 | Yamada | 564/54 X |

FOREIGN PATENT DOCUMENTS

| | | | |
|---|---|---|---|
| 0265162 | 10/1987 | European Pat. Off. | |
| 0050533 | 3/1985 | Japan | |
| 0921682 | 3/1963 | United Kingdom | 564/54 |
| 1437776 | 6/1976 | United Kingdom | |

Primary Examiner—William R. Dixon, Jr.
Assistant Examiner—James M. Hunter, Jr.
Attorney, Agent, or Firm—Joel G. Ackerman; Paul R. Martin

[57] ABSTRACT

An N,N-diaryl-N-alkylurea having the formula

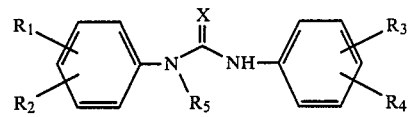

wherein $R_1$, $R_2$, $R_3$ and $R_4$ are the same or different and are selected from the group consisting of hydrogen, halogen, cyano, trifluoromethyl, trifluoromethylthio, trifluoromethyl thionyl, trifluoromethane sulfonyl, sulfonamido, substituted phenoxy and substituted pyridyloxy groups wherein the substituent is any one of halogen, cyano, trifluoromethyl, trifluoromethylthio, trifluoromethyl thionyl, trifluoromethane sulfonyl, sulfonamido; and $R_5$ is selected from the group consisting of alkyl, alkenyl, haloalkyl, haloalkenyl, hydroxyalkyl, hydroxyalkenyl, acetoxyalkyl, acetoxyalkenyl, mercaptoalkyl, and mercaptoalkenyl, wherein the alkyl or alkenyl group in each alkyl- or alkenyl-containing moiety has from 3 to 6 carbon atoms;

X is oxygen or sulfur;

and agriculturally acceptable salts thereof.

Also disclosed is an herbicidal composition and method of treating weeds.

18 Claims, No Drawings

N,N'-DIARYL-N-ALKYLUREAS AND METHOD OF USE

BACKGROUND OF THE INVENTION

The present invention relates to certain N,N'-diaryl-N-alkylurea herbicide compositions and methods of use.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil. Some herbicides are effective both as pre- and post-emergence herbicides. The N,N'-diaryl-N-alkylureas of this invention fall into that category.

The N,N'-diaryl-N-alkylurea compounds of this invention are bleaching herbicides. Bleaching herbicides are believed to be carotenoid synthesis inhibitors. Inhibition of carotene biosynthesis leads to the photodestruction of chlorophyll and thus prevents the plant from taking up nutrients from the air and soil. As a consequence, the leaves turn white and the plant dies.

THE PRIOR ART

Urea compounds as a general class are known to be herbicidally effective. An example of a urea compound having herbicidal activity is 1,1-dimethyl-3-(α,α,α-trifluoro-m-tolyl)urea. This compound is commonly known as fluometuron.

Additional urea compounds known in the art which are herbicidally effective include:
[m-(3,3-dimethylureido)phenyl tert-butyl carbamate] (karbutilate);
3-[p-(p-chlorophenoxy)phenyl]-1,1-dimethylurea (chloroxuron);
3-(3,4-dichlorophenyl)-1,1-dimethylurea (diuron);
N'-[5-(1,1-dimethylethyl)-3-isooxazolyl]-N,N-dimethylurea (isouron);
3-(hexahydro-4,7-methanoindan-5-yl)-1,1-dimethylurea (norea); and 1-(2-methylcyclohexyl)-3-phenylurea (siduron).

The foregoing compounds are separate and distinct from the ureas of the present invention.

DESCRIPTION OF THE INVENTION

It has now been discovered that certain N,N'-diaryl-N-alkylureas have good herbicidal and plant growth regulating activity, when applied either pre- or post-emergence and used against annual and perennial grasses and broadleaf weeds.

As used herein, the term "herbicide" means a compound or composition which adversely controls or modifies the growth of plants. By the term "herbicidally effective amount" is meant any amount of such compound or composition causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention are N,N'-diaryl-N-alkylureas having the following formula:

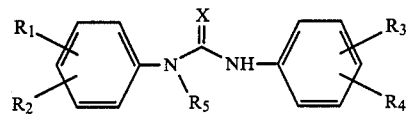

wherein $R_1$, $R_2$, $R_3$ and $R_4$ are the same or different and are selected from the group consisting of hydrogen, halogen, cyano, trifluoromethyl, trifluoromethylthio, trifluoromethyl thionyl, trifluoromethane sulfonyl, sulfonamido, substituted phenoxy and substituted pyridyloxy groups wherein the substituent is any one of haloge, cyano, trifluoromethyl, trifluoromethylthio, trifluoromethyl thionyl, trifluoromethane sulfonyl, sulfonamido; and $R_5$ is selected from the group consisting of alkyl, alkenyl, haloalkyl, haloalkenyl, hydroxyalkyl, hydroxylalkenyl, acetoxyalkyl, acetoxyalkenyl, mercaptoalkyl, and mercaptoalkenyl, wherein the alkyl or alkenyl group in each alkyl- or alkenyl-containing moiety has from 3 to 6 carbon atoms;

X is oxygen or sulfur;

and agriculturally acceptable salts thereof.

The compositions of the invention comprise the aforementioned herbicide compounds, along with inert diluent carriers, as set forth more fully hereinbelow.

The method of the invention comprises the application to the locus where control is desired of either the compound(s) or composition containing the compound(s) described herein.

Representative compounds falling within the scope of the formula as set forth above include:

N-(3-trifluoromethyl)phenyl-N-(2-mercapto)propyl-N'-(4-cyano)phenylurea hydrochloride N-(3-trifluoromethyl)phenyl-N-(2-mercapto)propyl-N'-(4-cyano)phenylurea N-(2-hydroxybutyl)-4-(3-trifluoromethyl)phenyl-N'-(4-cyano)phenylurea N-(2-chlorobutyl)-N-(3-trifluoromethyl)phenyl-N'-(4-cyano)phenylurea The compounds of this invention have been found to have especially good herbicidal activity against perennial and annual grasses and broadleaf weed species when applied as post-emergent herbicides.

The compounds of this invention can be made in a number of different ways, depending primarily upon the nature of the $R_5$ substitutent.

For example, when $R_5$ is an allyl (alkenyl) moiety, the compounds can be prepared by a multi-step reaction sequence which comprises reacting an allylanilide of the formula

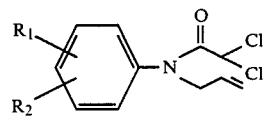

with a hydrolyzing agent to form an intermediate compound of the formula

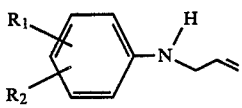

and in turn reacting the intermediate compound with an arylisocyanate or arylisothiocyanate of the formula

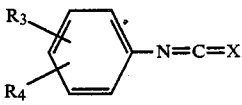

to achieve the desired product, wherein $R_1$–$R_4$ and X are as defined.

When $R_5$ is a crotyl (alkenyl) moiety, the compounds can be produced by reacting an anilide of the formula

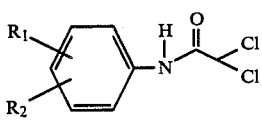

with sodium hydride, in the presence of crotyl bromide, to form a compound of the formula

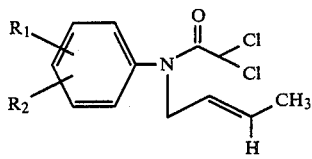

then hydrolyzing that compound to form compound of the formula

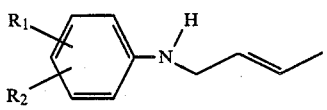

and in turn reacting that compound with an arylisocyanate or arylisothiocyanate of the formula

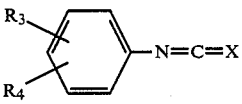

to produce the desired end product, where $R_1$–$R_4$ and X are also as previously defined.

When the $R_5$ substituent is an acetate moiety, the compound can be produced by reacting an anilino alcohol of the formula

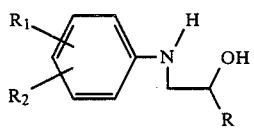

with an arylisocyanate or arylisothiocyanate of the formula

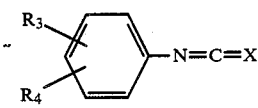

to form an intermediate compound of the formula

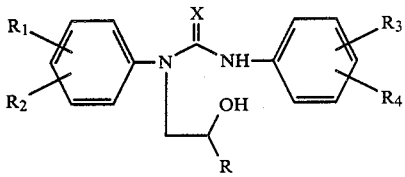

and in turn reacting this intermediate compound with acetyl chloride in the presence of pyridine or triethylamine to form an acetate of the formula

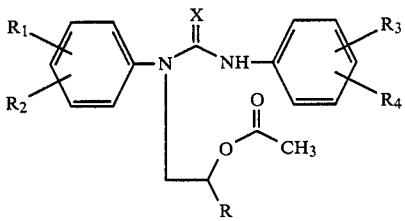

where $R_1$, $R_2$, $R_3$, $R_4$ and X are as previously defined and R is lower alkyl.

If the $R_5$ substituent is to be a halo substituted alkyl moiety, the compound can be produced by reacting an anilino alcohol of the formula

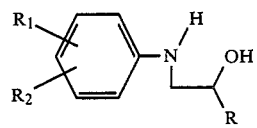

with an arylisocyanate or arylisothiocyanate of the formula

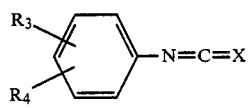

to produce an intermediate compound of the formula

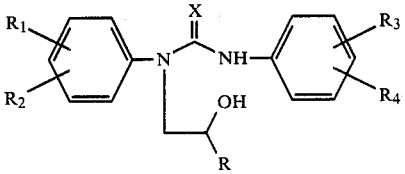

and in turn reacting this intermediate with thionyl chloride or thionyl bromide in a suitable organic solvent, to achieve the end product, a compound having the formula

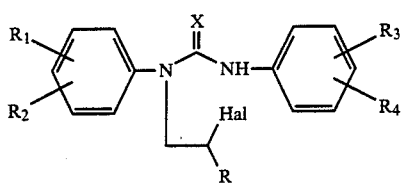

where $R_1$, $R_2$, $R_3$, $R_4$ and X are as previously defined and R is lower alkyl.

The starting compounds used in the process for preparing the compounds of the invention are either commercially available or known in the art.

For example, the anilino alcohols referred to above are described in co-pending U.S. patent application Ser. No. 864,238, filed May 19, 1986 (Attorney Docket PR-7625), and can be produced by condensation of an appropriate aniline with a suitable epoxide, as per the following reaction:

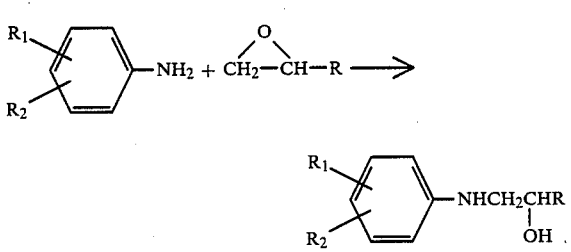

The allylamines used as starting compounds for making the allyl or crotyl substituted moieties of the urea compounds of this invention are described in U.S. Pat. No. 4,110,105.

The arylisocyanate or arylisothiocyanate compounds with which the starting compounds are reacted are also commercially available.

The process for making the compounds of this invention will be more fully understood by reference to the following examples.

EXAMPLE 1

Preparation of
N-Crotyl-N-(3-trifluoromethyl)phenyl-N'-(4-chloro-2-methyl)phenylthiourea To a one liter, three-necked round-bottomed flask equipped with a mechanical stirrer, pressure equalizing addition funnel and reflux condenser carrying a nitrogen bubbler was added 5.23 g (0.22 mole) of sodium hydride and 100 ml of tetrahydrofuran. The mixture was stirred and 54.41 g (0.20 mole) of m-trifluoromethyl dichloroacetanilide in 150 ml of tetrahydrofuran was added dropwise over a period of 0.5 hour. When the addition was complete, the stirring was continued until hydrogen evolution was completed (about 0.5 hour). At that time, 22.64 ml of crotyl bromide (0.22 mole) dissolved in 75 ml of tetrahydrofuran was then added dropwise with stirring over a period of 0.5 hour. When this addition was complete, the stirring was continued at room temperature for a period of approximately 16 hours. Thereafter, 10 ml of 3% aqueous hydrogen chloride was continuously added and stirred for 15 minutes. The solvent was then removed in vacuo and the residue partitioned between 300 ml ethylacetate and 200 ml of water. The organic phase then washed with 200 ml of water, followed by 200 ml of saturated sodium chloride.

The organic phase was dried over sodium sulfate and the solvent removed in vacuo to give 64.64 g (99%) of crude product having an amber-orange color, which was identified as N-crotyl-m-trifluoromethyl dichloroacetanilide.

The crude N-crotyl-m-trifluoromethyl dichloroacetanilide (64.64 g, 0.198 mol) and 300 ml of absolute ethanol were added to a round-bottomed flask, and stirred at room temperature, followed by the dropwise addition of 14.39 g of potassium hydroxide in 20 ml of water over a period of 10 minutes. After the addition was complete, the reaction mixture solidified with the precipitation of potassium dichloroacetate. The flask was swirled by hand to break up the solidified cake and stirring allowed to continue for an additional 18 hours. At the end of this time, 250 ml of ethyl acetate was added and the resulting mixture filtered. The solvent was then removed in vacuo to yield a pale orange-yellow semisolid. This was partitioned between 300 ml of ethyl acetate and 300 ml of water and separated. The organic layer was washed one time with 200 ml of water and one time with 200 ml of a saturated sodium chloride solution. The organic layer was then dried with sodium sulfate and the solvent removed in vacuo to yield a yellow-orange material that was distilled at aspirator pressure to yield 36.6 g (86%) of product, N-crotyl-m-trifluoromethyl aniline.

N-crotyl-m-trifluoromethyl aniline (7.10 g) was combined with 6.06 g of 4-chloro-2-methylphenylisothiocyanate in 20 ml of acetonitrile and approximately 100 mg of a catalyst, 1,4-diazobicyclo[2.2.2]-octane (DABCO). The reaction mixture was stirred for 24 hours and at the end of this time, 50 ml of ethylacetate was added. The solution was then washed 3 times with 25 ml of 3% aqueous hydrochloric acid. The organic phase was dried with sodium sulfate and the solvent removed in vacuo to yield 13.0 g (99%) of product. This was identified as N-crotyl-N-(3-trifluoromethyl)phenyl-N'(4-chloro-2-methyl)phenylthiourea.

EXAMPLE 2

Preparation of
N-(2-Hydroxybutyl)-N-(3-trifluoromethyl)phenyl-N'-(4-cyano)phenyl urea To a 250 ml round-bottomed flask were added 8.40 g (36.0 mmol) of 1-N-(m-trifluoromethylphenyl)amino-2-butanol, 5.19 g (36.0 mmol) of p-cyanophenylisocyanate, and 50 ml of acetonitrile. The isocyanate was introduced in a large lump and the resulting solution was stirred overnight at room temperature. At the end of this time, the reaction mixture had solidified. The material was then chilled in ice and the solid cake broken up with a spatula. It was then filtered and washed with 25 ml of ice-cooled acetonitrile and dried on a filter to yield 9.34 g (69%) of product as a white solid. The solid was identified as the subject compound by suitable analytical techniques.

EXAMPLE 3

Preparation of
N-Crotyl-N-(3-trifluoromethyl)phenyl-N'-(4-chloro)-phenylthiourea N-Crotyl-m-aminobenzotrifluoride (3.0 g, 13.9 mmol) prepared in accordance with the process described in Example 1 and 2.36 g (13.9 mmol) of 4-chlorophenylisothiocyanate were placed in a round-bottomed flask, along with approximately 100 mg of DABCO and 20 ml of acetonitrile. The mixture was allowed to stir at room temperature for approximately 21 hours, and then 100 ml of ethyl acetate was added. The contents were washed 3 times with 25 ml portions of 3% aqueous hydrochloric acid and dried over sodium sulfate to yield 5.36 g (100%) of product. This product was identified by suitable analytical techniques as being the subject compound.

EXAMPLE 4

Preparation of 1,3-Bis-4-trifluoromethylphenyl-1-allyl thiourea

A 100 ml round-bottomed flask equipped with a magnetic stirrer and a nitrogen bubbler was charged with 5.0 g (24.9 mmol) of N-allyl meta-aminobenzotrifluoride prepared in accordance with the process described in Example 1 and 5.06 g (24.9 mmol) of m-trifluoromethylphenyl isothiocyanate. One drop of dibutyl tin dilaurate catalyst was added and the mixture stirred at room temperature for 18 hours. The reaction mixture solidified yielding 9.58 g (95%) of product as a white solid which was identified as the subject compound by suitable analytical techniques.

EXAMPLE 5

Preparation of N-Allyl-N-(3-trifluoromethyl)phenyl-N'-(4-fluoro)-phenylurea

A round-bottomed flask equipped with a nitrogen bubbler and stirrer was charged with 5.0 g (24.9 mmol) of N-allyl-m-trifluoromethylphenylaniline and 3.41 g (24.9 mmol) of 4-fluoroisocyanate, and the mixture was allowed to stir at room temperature. The mixture exothermed to approximately 60° C. and then solidifed. After cooling to room temperature the solid material chipped out of the flask to give 8.35 g (99%) of product as a white solid, which was identified as the subject compound by suitable analytical techniques.

EXAMPLE 6

Preparation of N-(3-Trifluoromethyl)phenyl-N-(2-mercapto)-propyl-N'-(4-cyano)phenylurea hydrochloride A round-bottomed flask equipped with a nitrogen bubbler and mechanical stirrer was charged with 4.60 g (12.7 mmol) of N-allyl-N-(3-trifluoromethyl)phenyl-N'-(4-cyano)phenylthiourea and to this was added 50 ml of concentrated hydrochloride acid. The resultant oily suspension was heated on a steam bath with occasional swirling. After 20 minutes, the mixture had been converted to a yellow homogenous solution. The solution was filtered to remove a small amount of solid and 30 ml of water added. The resulting slightly turbid solution was extracted 3 times with 75 ml of methylene chloride, and the aqueous portion was split into two portions of 37.5 ml each. The water in one of those portions was removed in vacuo to give 2.18 g (86%) of the salt, N-(3-trifluoromethyl)phenyl-N-(2-mercapto)-propyl-N'-(4-cyano)phenylurea hydrochloride.

The other portion was neutralized with solid sodium bicarbonate and extracted with methylene chloride. The mixture was filtered through dicalite to break the emulsions. The methylene chloride extracts were combined, dried over $Na_2SO_4$ and the solvent removed in vacuo to yield 1.2 g (52%) of the base as an off-white solid.

EXAMPLE 7

Preparation of N-(2-Acetoxybutyl)-N-(3-trifluoromethyl)phenyl-N'-(4-cyano)phenylurea A round-bottomed flask equipped with a magnetic stirrer and nitrogen bubbler was charged with 2.00 g (5.3 mmol) of N-(2-hydroxybutyl)-N-(3-trifluoromethyl)phenyl-N'-(4-cyano)phenylurea urea (prepared in accordance with the process described in Example 2 herein) dissolved in 55 ml of methylene chloride. To this was added 0.74 ml triethylamine and 0.25 ml of acetyl chloride, in that order. The material only partially dissolved in the solvent, but became homogenous 30 seconds after the acetyl chloride was added. Thereafter, an additional 100 mol % of $CH_3COCl$ was added and the stirring continued. After 2 days the reaction appeared to have stopped. The solution was dissolved in a 1:1 ratio of ethyl acetate/hexanes, and the product isolated by chromtoagraphy using 40% EtOAC/60% hexanes to yield 1.48 g (47%) of the subject compound, as a colorless foam.

EXAMPLE 8

Preparation of N-(2-Chlorobutyl)-N-(3-trifluoromethyl)phenyl-N'-(4-cyano)phenylurea N-(2-Hydroxybutyl)-N-(3-trifluoromethyl)phenyl-N'-(4-cyano)phenylurea (5.0 g, 13.2 mmol), prepared in accordance with the method described in Example 2 hereof, was combined in a round bottomed flask with 75 ml of benzene and 1.44 ml (19.8 mmol) of thionyl chloride. The resulting solution was heated to refluxing for 1.5 hr under nitrogen and magnetic stirring. The volatile ingredients were then removed in vacuo, to yield 5.42 g (99%) of the product, a stiff pink foam, which was identified as the subject compound by conventional analytical techniques.

EXAMPLE 9

Preparation of N-(Crotyl)-N-(3-trifluoromethyl)phenyl-N'-(4-chloro)-benzylthiourea N-Crotyl-m-aminobenzotrifluoride (5.86 g, 27.2 mmol) and 5.0 g (27.2 mmol) of 4-chlorobenzylisothiocyanate was charged into a round-bottomed flask equipped with a magnetic stirrer and nitrogen bubbler, along with approximately 100 mg of DABCO, and 20 ml of acetonitrile. The mixture was allowed to stir at room temperature for approximately 80 hours. Ethyl acetate (100 ml) was added to the reaction mixture and the resulting solution was washed three times with 25 ml of 3% hydrochloric acid and dried over sodium sulfate. Removal of the solvent in vacuo provided 10.86 g (100%) of product, which was identified by suitable analytical techniques as being the subject compound.

EXAMPLE 10

Preparation of N-(Crotyl)-N-(3-trifluoromethyl)phenyl-N'-(3-trifluoromethyl)phenylthiourea N-Crotyl-m-aminobenzotrifluoride (4.66 g, 21.7 mmol) and 4.40 g (21.7 mmol) of m-trifluoromethylphenyl isothiocyanate were added to a round-bottomed flask equipped with a magnetic stirrer and nitroge bubbler. After stirring at room temperature for approximately 2 hours one drop of dibutyl tin dilaurate was added. The mixture was stirred for approximately 2 days and became so thick that the stirring was stopped. The crude reaction mixture was then chromatographed on a silica column with 2:1 methylene chloride/hexanes to give 7.05 g (78%) of product, a pale yellow syrup, which was identified as the subject compound by suitable analytical techniques.

When produced, the compounds of this invention are of a basic nature. The compounds can be reacted with strong acids to produce an agriculturally acceptable salt as is exemplified in Example 6 herein, wherein the hydrochloride salt of the compound was initially produced. Strong acid salts could also be made from sulfuric or phosphoric acid, for example. Therefore, any reference to the compound in the specification and claims is intended to encompass the agriculturally acceptable salts thereof within its purview.

These and other compounds made by the foregoing processes are set forth in Table I which follows, wherein the various substituent groups are indicated.

TABLE I

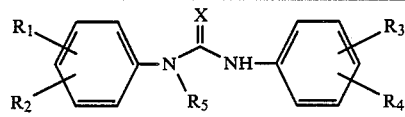

| Cmpd. No. | $R_1$ | $R_2$ | $R_3$ | $R_4$ | $R_5$ | X | Physical Constant m.p. °C. or $n_D^{30}$ |
|---|---|---|---|---|---|---|---|
| 1 | H | 3-$CF_3$ | H | 4-F | $CH_2CH=CH_2$ | S | 88.0–91.0 |
| 2 | H | 3-$CF_3$ | H | 4-CN | $CH_2CHSHCH_3$ | S | 192.0–200.0 |
| 3 | H | 3-$CF_3$ | H | 4-CN | $CH_2CHSHCH_3$ | O | hygroscopic glass |
| 4 | H | 3-$CF_3$ | H | 4-CN | $CH_2CH=CH_2$ | O | thick syrup |
| 5 | H | 3-$CF_3$ | H | 2-Cl | $CH_2CH=CH_2$ | S | thick syrup |
| 6 | H | 3-$CF_3$ | H | 3-Cl | $CH_2CH=CH_2$ | S | 59.0–61.0 |
| 7 | H | 3-$CF_3$ | H | 3-$NO_2$ | $CH_2CH=CH_2$ | S | 102.5–106.0 |
| 8 | H | 3-$CF_3$ | H | 3-F | $CH_2CH=CH_2$ | S | 60.5–62.5 |
| 9 | H | 3-$CF_3$ | H | 4-$NO_2$ | $CH_2CH=CH_2$ | S | 93.5–102.5 |
| 10 | H | 3-$CF_3$ | H | 4-Cl | $CH_2CH=CH_2$ | S | 92.0–93.0 |
| 11 | H | 3-$CF_3$ | H | 2-F | $CH_2CH=CH_2$ | S | thick syrup |
| 12 | H | 3-$CF_3$ | 3-$CF_3$ | 4-Cl | $CH_2CH=CH_2$ | S | thick syrup |
| 13 | H | 3-$CF_3$ | 4-$CH_3$ | 2-Cl | $CH_2CH=CH_2$ | S | 74.5–76.0 |
| 14 | H | 3-$CF_3$ | H | 5-F | $CH_2CH=CH_2$ | S | thick syrup |
| 15 | H | 3-$CF_3$ | H | 4-F | $CH_2CH=CH_2$ | S | thick syrup |
| 16 | H | 3-$CF_3$ | H | 3-$CF_3$ | $CH_2CH=CHCH_3$ | S | thick syrup |
| 17 | H | 3-$CF_3$ | H | 4-CN | $CH_2CH=CHCH_3$ | S | thick syrup |
| 18 | H | 3-$CF_3$ | H | 3-F | $CH_2CH=CHCH_3$ | S | thick syrup |
| 19 | H | 3-$CF_3$ | H | 3-Cl | $CH_2CH=CHCH_3$ | S | 44.0–64.0 |
| 20 | H | 3-$CF_3$ | H | 4-$NO_2$ | $CH_2CH=CHCH_3$ | S | thick syrup |
| 21 | H | 3-$CF_3$ | H | 3-CN | $CH_2CH=CHCH_3$ | S | thick syrup |
| 22 | H | 3-$CF_3$ | H | 4-Cl | $CH_2CH=CHCH_3$ | S | thick syrup |
| 23 | H | 3-CN | H | 4-Cl | $CH_2CH=CHCH_3$ | S | 112.0–118.0 |
| 24 | H | 3-CN | H | 4-CN | $CH_2CH=CHCH_3$ | S | 105.0–112.0 |
| 25 | H | 3-Cl | H | 4-CN | $CH_2CH=CHCH_3$ | S | 83.0–91.0 |
| 26 | H | 3-$CF_3$ | H | 4-F | $CH_2CH=CHCH_3$ | S | thick syrup |
| 27 | H | 3-$CF_3$ | 2-Cl | 4-Cl | $CH_2CH=CHCH_3$ | S | thick syrup |
| 28 | H | 3-$CF_3$ | 3-Cl | 5-Cl | $CH_2CH=CHCH_3$ | S | thick syrup |
| 29 | H | 3-$CF_3$ | 3-Cl | 4-Cl | $CH_2CH=CHCH_3$ | S | 77.0–83.0 |
| 30 | H | 3-$CF_3$ | 3-Cl | 4-F | $CH_2CH=CHCH_3$ | S | thick syrup |
| 31 | H | 3-$CF_3$ | 3-$CF_3$ | 4-Cl | $CH_2CH=CHCH_3$ | S | thick syrup |
| 32 | H | 3-$CF_3$ | 2-$CH_3$ | 4-Cl | $CH_2CH=CHCH_3$ | S | 1.5918 |
| 33 | H | 3-CN | H | 3-Cl | $CH_2CH=CHCH_3$ | S | 107.0–111.0 |
| 34 | H | 3-Cl | 3-Cl | 4-Cl | $CH_2CH=CHCH_3$ | S | thick syrup |
| 35 | H | 3-Cl | 3-$CF_3$ | 4-Cl | $CH_2CH=CHCH_3$ | S | thick syrup |
| 36 | H | 3-$CF_3$ | H | 4-$CF_3$ | $CH_2CH=CHCH_3$ | S | thick syrup |
| 37 | H | 3-$CF_3$ | H | 3-Br | $CH_2CH=CHCH_3$ | S | waxy solid |
| 38 | H | 3-Cl | H | 3-Br | $CH_2CH=CHCH_3$ | S | thick syrup |
| 39 | H | 3-$CF_3$ | H | 3-$NO_2$ | $CH_2CH=CHCH_3$ | S | thick syrup |
| 40 | H | 3-$CF_3$ | H | 4-Br | $CH_2CH=CHCH_3$ | S | thick syrup |
| 41 | H | 3-$CF_3$ | 3-Cl | 4-Br | $CH_2CH=CHCH_3$ | S | 80.0–87.0 |
| 42 | H | 3-$CF_3$ | H | 4-Cl | $CH_2CH=CHCH_3$ | S | thick syrup |
| 43 | H | 3-Cl | H | 4-Cl | $CH_2CH=CHCH_3$ | S | thick syrup |
| 44 | H | 3-$CF_3$ | H | 4-CN | $CH_2CHOHCH_2CH_3$ | O | 167.0–169.0 |
| 45 | H | 3-$CF_3$ | H | 4-CN | $CH_2CHClCH_2CH_3$ | O | 102.0–105.0 |
| 46 | H | 3-$CF_3$ | H | 4-CN | $CH_2CHOHCH_3$ | O | 170.0–171.0 |
| 47 | H | 3-$CF_3$ | H | 4-CN | $CH_2CHClCH_3$ | O | 134.0–138.0 |
| 48 | H | 3-$CF_3$ | H | 4-CN | $CH_2CHOAcCH_2CH_3$* | O | thick syrup |
| 49 | H | 3-$CF_3$ | H | 4-F | $CH_2CHOHCH_2CH_3$ | O | 142.0–145.0 |
| 50 | H | 3-$CF_3$ | H | 4-F | $CH_2CHClCH_2CH_3$ | O | 139.0–140.0 |
| 51 | H | 3-$CF_3$ | H | 3-$NO_2$ | $CH_2CHOHCH_2CH_3$ | O | thick syrup |
| 52 | H | 3-$CF_3$ | H | 4-$NO_2$ | $CH_2CHOHCH_2CH_3$ | O | 152.0–153.5 |
| 53 | H | 3-$CF_3$ | H | 4-$NO_2$ | $CH_2CHOAcCH_2CH_3$ | O | 131.0–134.0 |
| 54 | H | 3-$CF_3$ | H | 2-F | $CH_2CHClCH_2CH_3$ | O | thick syrup |
| 55 | H | 3-$CF_3$ | H | 3-$NO_2$ | $CH_2CHClCH_2CH_3$ | O | 83.0–91.0 |
| 56 | H | 3-$CF_3$ | H | 3-$NO_2$ | $CH_2CHOAcCH_2CH_3$ | O | 135.0–140.0 |
| 57 | H | 3-$CF_3$ | H | 2-F | $CH_2CHOHCH_2CH_3$ | O | thick syrup |
| 58 | H | 3-$CF_3$ | H | 3-F | $CH_2CHClCH_2CH_3$ | O | 83.0–87.0 |
| 59 | H | 3-$CF_3$ | 3-Cl | 4-F | $CH_2CHClCH_2CH_3$ | O | 130.0–135.0 |
| 60 | H | 3-$CF_3$ | 3-Cl | 4-F | $CH_2CHOHCH_2CH_3$ | O | 120.0–125.0 |

TABLE I-continued

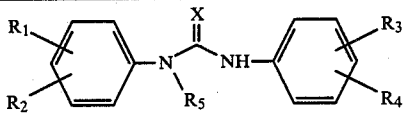

| Cmpd. No. | R₁ | R₂ | R₃ | R₄ | R₅ | X | Physical Constant m.p. °C. or $n_D^{30}$ |
|---|---|---|---|---|---|---|---|
| 61 | H | 3-CF₃ | 3-F | H | CH₂CHOHCH₂CH₃ | O | 82.0–89.0 |
| 62 | H | 3-CF₃ | 3-F | H | CH₂CHOAcCH₂CH₃ | O | 101.0–108.0 |
| 63 | H | 3-CF₃ | 2-F | H | CH₂CHOAcCH₂CH₃ | O | 58.0–66.0 |
| 64 | H | 3-CF₃ | 4-SCH₃ | H | CH₂CHOHCH₂CH₃ | O | 107.0–112.0 |
| 65 | H | 3-CF₃ | 3-SCH₃ | H | CH₂CHOHCH₂CH₃ | O | 88.0–91.5 |
| 66 | H | 3-CF₃ | H | 4-COCH₃ | CH₂CHClCH₂CH₃ | O | thick syrup |
| 67 | H | 3-CF₃ | H | 4-COCH₃ | CH₂CHOHCH₂CH₃ | O | 117.0–121.0 |
| 68 | H | 3-CF₃ | H | 4-COCH₃ | CH₂CHOAcCH₂CH₃ | O | thick syrup |
| 69 | H | 3-CF₃ | 3-Cl | 4-F | CH₂CHOAcCH₂CH₃ | O | 112.0–119.0 |
| 70 | H | 3-CF₃ | 3-SCH₃ | H | CH₂CHOAcCH₂CH₃ | O | thick syrup |

*The designation "Ac" refers to an acetyl moiety.

The herbicidal activity of representative compounds of the invention is exhibited by means of tests in accordance with the following procedures.

HERBICIDAL ACTIVITY TESTS

Test No. 1

This test offers herbicidal activity test data to show the effectiveness of the compounds of the invention against various weed species. The effect is observed by comparing the extent of weed control in test flats treated with the compounds against that occurring in similar control flats. All are applied at 4.0 lb/A (4.48 kg/ha) to a pre-emergence and a post-emergence screening flat. An 80 gal/A (748.3 l/ha) spray volume is utilized. Post-emergence flats are seeded 12 days prior to treatment. Pre-emergence flats are seeded one day prior to treatment. Overhead watering of pre-emergence flats and soil surface watering of post-emergence flats, so as to avoid wetting the foliage, is carried out for the duration of the test.

Weed seeds are planted in a 6×10×3 inch (15.25×7.6 cm) aluminum flat at a seed depth of 0.5 inch (1.3 cm). Soil for flats is prepared using Keeton sandy loam soil fortified with 17-17-17 fertilizer

| COMMON NAME | SCIENTIFIC NAME | ABR |
|---|---|---|
| Broadleaf Weeds: | | |
| annual morningglory | Ipomoea purpurea | AMG |
| velvetleaf | Abutilon theophrasti | VL |
| mustard | Brassica sp. | MD |
| curly dock | Rumex crispus | CD |
| Grasses: | | |
| yellow nutsedge | Cyperus exculentus | YNS |
| foxtail | Setaria sp. | FT |
| watergrass | Echinochloa crusgalli | WG |
| wild oat | Avena fatua | WO |

The spray solution is prepared by dissolving 240 mg of herbicide compound in 20 ml of acetone containing 1% Tween®20 (polyoxy ethylene sorbitan monolaurate), then adding 20 ml of water to the resulting solution. The stock solutions are applied using a linear spray table. The table is calibrated to deliver 80 gal/A (748.3 l/ha) of spray solution using an 8004E teejet nozzle set 18 inches (45.7 cm) from the surface. Pre-emergence flats are raised to the level of the post-emergence foliage canopy by setting the flats on a wooden block.

In both instances, either pre- or post-emergent testing, approximately 18 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Table below.

TABLE II

| Cmpd. No. | Application Rate (lb/A) | Method | GREENHOUSE HERBICIDE TEST RESULTS | | | | | | | |
|---|---|---|---|---|---|---|---|---|---|---|
| | | | SETVI | ECHCG | AVEFA | PHBPU | ABUTH | SINAR | CUMCR | CYPES |
| | | | \multicolumn{8}{c}{Percent Injury} | | | | | | | |
| | | | FT | WG | WO | AMG | VL | MD | CD | YNS |
| 1 | 4.00 | PES | 0 | 0 | 0 | 0 | 0 | 0 | — | 0 |
| | 4.00 | POS | 0 | 0 | 0 | 0 | 20 | 50 | — | 0 |
| 2 | 4.00 | PES | 90 | 75 | 35 | 100 | 50 | 100 | 70 | 0 |
| | 4.00 | POS | 25 | 25 | 25 | 40 | 75 | N | 50 | 0 |
| 3 | 4.00 | PES | 85 | 70 | 25 | 25 | 40 | 90 | 100 | 0 |
| | 4.00 | POS | 25 | 20 | 15 | 35 | 30 | 25 | 50 | 0 |
| 4 | 4.00 | PES | 75 | 25 | 25 | 25 | 25 | 95 | 100 | 0 |
| | 4.00 | POS | 10 | 10 | 10 | 20 | 25 | 90 | 50 | 0 |
| 5 | 4.00 | PES | 0 | 0 | 0 | 0 | 0 | 0 | 0 | 0 |
| | 4.00 | POS | 0 | 0 | 0 | 0 | 0 | 10 | 0 | 0 |
| 6 | 4.00 | PES | 65 | 0 | 0 | 0 | 0 | 15 | 95 | 0 |
| | 4.00 | POS | 0 | 0 | 0 | 35 | 10 | 85 | 85 | 0 |
| 7 | 4.00 | PES | 0 | 0 | 0 | 0 | 0 | 0 | 0 | 0 |
| | 4.00 | POS | 0 | 0 | 0 | 35 | 35 | 40 | 50 | 0 |
| 8 | 4.00 | PES | 0 | 0 | 0 | 0 | 0 | 0 | 0 | 0 |
| | 4.00 | POS | 0 | 0 | 0 | 35 | 30 | 65 | 0 | 0 |

TABLE II-continued
GREENHOUSE HERBICIDE TEST RESULTS

| Cmpd. No. | Application Rate (lb/A) | Method | SETVI FT | ECHCG WG | AVEFA WO | PHBPU AMG | ABUTH VL | SINAR MD | CUMCR CD | CYPES YNS |
|---|---|---|---|---|---|---|---|---|---|---|
| 9  | 4.00 | PES | 35  | 40 | 0  | 20  | 35  | 50  | 20  | 0 |
|    | 4.00 | POS | 0   | 0  | 0  | 20  | 10  | 30  | 10  | 0 |
| 10 | 4.00 | PES | 50  | 0  | 0  | 0   | 0   | 20  | 100 | 0 |
|    | 4.00 | POS | 0   | 0  | 0  | 40  | 50  | 75  | 50  | 0 |
| 11 | 4.00 | PES | 0   | 0  | 0  | 0   | 0   | 0   | 0   | 0 |
|    | 4.0. | POS | 25  | 35 | 0  | 35  | 40  | 80  | 85  | 0 |
| 12 | 4.00 | PES | 50  | 0  | 0  | 0   | 0   | 35  | 100 | 0 |
|    | 4.00 | POS | 35  | 40 | 10 | 20  | 70  | 80  | 100 | 0 |
| 13 | 4.00 | PES | 50  | 0  | 0  | 0   | 0   | 20  | 100 | 0 |
|    | 4.00 | POS | 40  | 10 | 10 | 20  | 40  | 70  | 95  | 0 |
| 14 | 4.00 | PES | 0   | 0  | 0  | 0   | 0   | 0   | 0   | 0 |
|    | 4.00 | POS | 40  | 40 | 20 | 35  | 75  | 20  | 60  | 0 |
| 15 | 4.00 | PES | 90  | 30 | 20 | 90  | 20  | 90  | —   | 0 |
|    | 4.00 | POS | 60  | 30 | 10 | 80  | 80  | 80  | —   | 0 |
| 16 | 4.00 | PES | 35  | 0  | 0  | 0   | 0   | 35  | 90  | 0 |
|    | 4.00 | POS | 0   | 0  | 0  | 60  | 35  | 90  | 20  | 0 |
| 17 | 4.00 | PES | 70  | 70 | 0  | 20  | 10  | 30  | 0   | 0 |
|    | 4.00 | POS | 25  | 25 | 20 | 35  | 20  | 40  | 35  | N |
| 18 | 4.00 | PES | 0   | 0  | 0  | 0   | 0   | 0   | 0   | 0 |
|    | 4.00 | POS | 0   | 0  | 0  | 20  | 25  | 50  | 0   | 0 |
| 19 | 4.00 | PES | 100 | 70 | 25 | 30  | 30  | 80  | 35  | 0 |
|    | 4.00 | POS | 40  | 40 | 35 | 65  | 60  | 70  | 50  | 0 |
| 20 | 4.00 | PES | 0   | 0  | 0  | 30  | 35  | 30  | 0   | 0 |
|    | 4.00 | POS | 25  | 20 | 0  | 0   | 0   | 50  | 0   | 0 |
| 21 | 4.00 | PES | 0   | 0  | 0  | 25  | 20  | 95  | —   | 0 |
|    | 4.00 | POS | 20  | 0  | 0  | 25  | 50  | 80  | —   | 0 |
| 22 | 4.00 | PES | 0   | 0  | 0  | 0   | 0   | 50  | —   | 0 |
|    | 4.00 | POS | 0   | 0  | 0  | 20  | 100 | 75  | —   | 0 |
| 23 | 4.00 | PES | 40  | 5  | 0  | 0   | 0   | 10  | —   | 0 |
|    | 4.00 | POS | 5   | 30 | 0  | 10  | 30  | 80  | —   | 0 |
| 24 | 4.00 | PES | 95  | 50 | 0  | 5   | 30  | 90  | —   | 0 |
|    | 4.00 | POS | 10  | 20 | 0  | 40  | 30  | 60  | —   | 0 |
| 25 | 4.00 | PES | 100 | 60 | 90 | 40  | 90  | 100 | —   | 0 |
|    | 4.00 | POS | 10  | 40 | 10 | 40  | 40  | 85  | —   | 0 |
| 26 | 4.00 | PES | 100 | 30 | 0  | 60  | 85  | 100 | —   | 0 |
|    | 4.00 | POS | 10  | 40 | 0  | 10  | 80  | 80  | —   | 0 |
| 27 | 4.00 | PES | 0   | 5  | 0  | 0   | 0   | 0   | —   | 0 |
|    | 4.00 | POS | 5   | 0  | 0  | 10  | 20  | 90  | —   | 0 |
| 28 | 4.00 | PES | 0   | 0  | 0  | 0   | 5   | 0   | —   | 0 |
|    | 4.00 | POS | 10  | 0  | 0  | 10  | 40  | 80  | —   | 0 |
| 29 | 4.00 | PES | 40  | 0  | 0  | 10  | 10  | 90  | —   | 0 |
|    | 4.00 | POS | 10  | 5  | 5  | 10  | 70  | 80  | —   | 0 |
| 30 | 4.00 | PES | 65  | 5  | 0  | 5   | 20  | 95  | —   | 0 |
|    | 4.00 | POS | 20  | 5  | 5  | 10  | 90  | 80  | —   | 0 |
| 31 | 4.00 | PES | 10  | 0  | 0  | 0   | 0   | 100 | —   | 0 |
|    | 4.00 | POS | 40  | 10 | 0  | 20  | 30  | 90  | —   | 0 |
| 32 | 4.00 | PES | 5   | 5  | 0  | 10  | 20  | 100 | —   | 0 |
|    | 4.00 | POS | 10  | 5  | 10 | 10  | 60  | 70  | —   | 0 |
| 33 | 4.00 | PES | 0   | 0  | 0  | 0   | 0   | 0   | —   | 0 |
|    | 4.00 | POS | 5   | 0  | 0  | 5   | 10  | 85  | —   | 0 |
| 34 | 4.00 | PES | 0   | 0  | 0  | 0   | 0   | 10  | —   | 0 |
|    | 4.00 | POS | 70  | 0  | 0  | 5   | 30  | 65  | —   | 0 |
| 35 | 4.00 | PES | 10  | 0  | 0  | 0   | 5   | 80  | —   | 0 |
|    | 4.00 | POS | 50  | 0  | 0  | 5   | 20  | 80  | —   | 0 |
| 36 | 4.00 | PES | 98  | 5  | 10 | 20  | 100 | 98  | —   | 0 |
|    | 4.00 | POS | 90  | 10 | 0  | 20  | 80  | 80  | —   | 0 |
| 37 | 4.00 | PES | 75  | 10 | 10 | 45  | 90  | 95  | —   | 0 |
|    | 4.00 | POS | 20  | 10 | 0  | 10  | 80  | 80  | —   | 0 |
| 38 | 4.00 | PES | 5   | 0  | 0  | 5   | 10  | 5   | —   | 0 |
|    | 4.00 | POS | 20  | 0  | 0  | 10  | 20  | 50  | —   | 0 |
| 39 | 4.00 | PES | 90  | 20 | 10 | 20  | 20  | 100 | —   | N |
|    | 4.00 | POS | 50  | 50 | 20 | 10  | 50  | 90  | —   | 0 |
| 40 | 4.00 | PES | 90  | 5  | 5  | 20  | 80  | 100 | —   | N |
|    | 4.00 | POS | 20  | 0  | 5  | 10  | 50  | 65  | —   | 0 |
| 41 | 4.00 | PES | 30  | 0  | 0  | 5   | 10  | 90  | —   | 0 |
|    | 4.00 | POS | 20  | 5  | 0  | 10  | 80  | 80  | —   | 0 |
| 42 | 4.00 | PES | 30  | 0  | 0  | 10  | 50  | 90  | —   | 0 |
|    | 4.00 | POS | 0   | 0  | 0  | 5   | 5   | 30  | —   | 0 |
| 43 | 4.00 | PES | 5   | 5  | 0  | 0   | 0   | 0   | —   | 0 |
|    | 4.00 | POS | 0   | 0  | 0  | 0   | 0   | 0   | —   | 0 |
| 44 | 4.00 | PES | 0   | 0  | 0  | 5   | 5   | 5   | —   | 0 |
|    | 4.00 | POS | 0   | 0  | 0  | 0   | 0   | 0   | —   | 0 |
| 45 | 4.00 | PES | 100 | 85 | 80 | 100 | 98  | 100 | —   | 0 |
|    | 4.00 | POS | 75  | 80 | 80 | 50  | 100 | 80  | —   | 10 |
| 46 | 4.00 | PES | 30  | 5  | 0  | 10  | 20  | 90  | —   | 0 |
|    | 4.00 | POS | 0   | 0  | 0  | 5   | 5   | 5   | —   | 0 |
| 47 | 4.00 | PES | 100 | 80 | 70 | 90  | 100 | 100 | —   | 0 |

TABLE II-continued
GREENHOUSE HERBICIDE TEST RESULTS

| Cmpd. No. | Application Rate (lb/A) | Method | SETVI FT | ECHCG WG | AVEFA WO | PHBPU AMG | ABUTH VL | SINAR MD | CUMCR CD | CYPES YNS |
|---|---|---|---|---|---|---|---|---|---|---|
|  | 4.00 | POS | 80 | 80 | 30 | 25 | 100 | 95 | — | N |
| 48 | 4.00 | PES | 100 | 80 | 70 | 90 | 95 | 95 | — | 0 |
|  | 4.00 | POS | 50 | 50 | 50 | 50 | 80 | 80 | — | N |
| 49 | 4.00 | PES | 5 | 0 | 0 | 0 | 0 | 0 | — | 0 |
|  | 4.00 | POS | 0 | 0 | 0 | 5 | 0 | 10 | — | 0 |
| 50 | 4.00 | PES | 100 | 100 | 85 | 100 | 100 | 100 | — | 0 |
|  | 4.00 | POS | 90 | 80 | 80 | 80 | 100 | 90 | — | 0 |
| 51 | 4.00 | PES | 90 | 20 | 10 | 10 | 30 | 95 | — | 0 |
|  | 4.00 | POS | 5 | 10 | 10 | 10 | 10 | 50 | — | 0 |
| 52 | 4.00 | PES | 10 | 5 | 0 | 5 | 0 | 90 | — | 0 |
|  | 4.00 | POS | 0 | 0 | 0 | 10 | 0 | 10 | — | 0 |
| 53 | 4.00 | PES | 0 | 0 | 0 | 5 | 5 | 0 | — | 0 |
|  | 4.00 | POS | 0 | 0 | 0 | 10 | 0 | 40 | — | 0 |
| 54 | 4.00 | PES | 100 | 40 | 10 | 0 | 0 | 50 | — | 0 |
|  | 4.00 | POS | 50 | 10 | 10 | 10 | 100 | 100 | — | 0 |
| 55 | 4.00 | PES | 90 | 10 | 20 | 20 | 20 | 50 | — | 0 |
|  | 4.00 | POS | 10 | 10 | 0 | 10 | 80 | 80 | — | 0 |
| 56 | 4.00 | PES | 0 | 0 | 0 | 0 | 0 | 0 | — | 0 |
|  | 4.00 | POS | 0 | 0 | 0 | 5 | 5 | 10 | — | 0 |
| 57 | 4.00 | PES | 50 | 0 | 0 | 0 | 0 | 0 | — | 0 |
|  | 4.00 | POS | 0 | 0 | 0 | 5 | 10 | 10 | — | 0 |
| 58 | 4.00 | PES | 100 | 80 | 70 | 50 | 80 | 100 | — | 0 |
|  | 4.00 | POS | 20 | 40 | 20 | 80 | 80 | 80 | — | 0 |
| 59 | 4.00 | PES | 80 | 10 | 10 | 10 | 80 | 90 | — | 0 |
|  | 4.00 | POS | 10 | 10 | 10 | 40 | 70 | 90 | — | 0 |
| 60 | 4.00 | PES | 0 | 0 | 0 | 0 | 0 | 0 | — | 0 |
|  | 4.00 | POS | 5 | 0 | 0 | 0 | 5 | 5 | — | 0 |
| 61 | 4.00 | PES | 85 | 40 | 20 | 20 | 90 | 100 | — | 30 |
|  | 4.00 | POS | 30 | 30 | 30 | 20 | 40 | 80 | — | 0 |
| 62 | 4.00 | PES | 50 | 20 | 10 | 0 | 80 | 95 | — | 70 |
|  | 4.00 | POS | 10 | 30 | 10 | 5 | 5 | 20 | — | 30 |
| 63 | 4.00 | PES | 20 | 10 | 0 | 0 | 80 | 90 | — | 0 |
|  | 4.00 | POS | 5 | 0 | 0 | 0 | 10 | 10 | — | 0 |
| 64 | 4.00 | PES | 0 | 0 | 0 | 0 | 0 | 0 | — | 0 |
|  | 4.00 | POS | 0 | 0 | 0 | 0 | 0 | 0 | — | 0 |
| 65 | 4.00 | PES | 10 | 0 | 0 | 0 | 0 | 0 | — | 0 |
|  | 4.00 | POS | 10 | 0 | 0 | 0 | 30 | 0 | — | 0 |
| 66 | 4.00 | PES | 80 | 10 | 0 | 0 | 10 | 0 | — | 0 |
|  | 4.00 | POS | 10 | 20 | 10 | 10 | 30 | 50 | — | 0 |
| 67 | 4.00 | PES | 0 | 10 | 10 | 5 | 0 | 80 | — | 0 |
|  | 4.00 | POS | 0 | 0 | 0 | 25 | 0 | 50 | — | 0 |
| 68 | 4.00 | PES | 0 | 0 | 0 | 0 | 0 | 0 | — | 0 |
|  | 4.00 | POS | 0 | 0 | 0 | 0 | 0 | 0 | — | 0 |
| 69 | 4.00 | PES | 0 | 0 | 0 | 0 | 0 | 0 | — | 0 |
|  | 4.00 | POS | 5 | 0 | 0 | 0 | 0 | 5 | — | 0 |
| 70 | 4.00 | PES | 10 | 0 | 0 | 0 | 0 | 0 | — | 0 |
|  | 4.00 | POS | 5 | 5 | 10 | 10 | 10 | — | 0 |  |

A dash (—) indicates not tested.

Test No. 2

Another series of tests was undertaken in accordance with the procedure described above in Test 1, except that differing quantities of herbicide were used. Those quantities were achieved by dilution of the original spray solution.

The weeds species were as follows:

| | | |
|---|---|---|
| green foxtail | Setaria viridis | FT |
| annual ryegrass | Lolium multiflorum | ARG |
| watergrass | Echinochloa crusgalli | WG |
| shattercane | Sorghum bicolor | SHC |
| wild oat | Avena fatua | WO |
| broadleaf signalgrass | Brachiaria platyphylla | BSG |
| annual morningglory | Ipomoea purpurea | AMG |
| cocklebur | Xanthium pensylvanicum | CB |
| hemp sesbania | (Sesbania exaltata) | SESB |
| velvetleaf | Abutilon theophrasti | VL |
| sicklepod | Cassia obtusifolia | SP |
| yellow nutsedge | Cyperus esculentus | YNS |

In addition to the foregoing weed species, the herbicides were also tested against various crop species. The crop species were as follows:

| | | |
|---|---|---|
| soybean | Glycine max | SOY |
| milo | Sorghum bicolor | ML |
| rice | Oryzae sativa | RC |
| sugarbeet | Beta vulgaris | SB |
| corn | Zea mays | CN |
| cotton | Gossypium hirsutum | COT |
| wheat | Triticum aestivum | WH |

The results of these tests are set forth in Table III below.

TABLE III

| Cmpd. No. | Application Rate lb/A | Method | FT | ARG | WG | SHC | WO | BSG | AMG | CB | SESB | VL | SP | YNS | SOY | WH | ML | RC | SB | CN | COT |
|---|---|---|---|---|---|---|---|---|---|---|---|---|---|---|---|---|---|---|---|---|---|
| 2 | 2.00 | PES | 100 | 100 | 100 | 70 | 45 | 100 | 100 | 100 | 100 | 100 | 100 | 0 | 65 | 15 | 70 | 35 | 100 | 60 | 40 |
|   | 1.00 | PES | N | N | N | N | N | N | 100 | 25 | 100 | 100 | 100 | 0 | 25 | 10 | 45 | 30 | 100 | 40 | 40 |
|   | 0.50 | PES | N | N | N | N | N | N | 75 | N | 100 | 0 | 100 | 0 | 15 | 10 | 40 | 30 | 100 | 30 | 15 |
| 8 | 0.10 | POS | N | N | N | N | N | N | 0 | 0 | 0 | 0 | 0 | 0 | 0 | 0 | 0 | 0 | 0 | 0 | 0 |
|   | 0.25 | POS | 0 | 0 | 0 | 0 | 0 | 0 | 0 | 0 | 0 | 0 | 0 | 0 | 0 | 0 | 0 | 0 | 0 | 0 | 0 |
|   | 0.50 | POS | 0 | 0 | 0 | 0 | 0 | 0 | 0 | 0 | 5 | 20 | 0 | 0 | 0 | 0 | 0 | 0 | 0 | 0 | 0 |
|   | 1.00 | POS | 0 | 0 | 0 | 0 | 0 | 0 | 10 | 0 | 0 | 0 | 5 | 0 | 10 | 0 | 0 | 0 | 5 | 0 | 5 |
| 22 | 0.25 | PES | 5 | 0 | 0 | 5 | 5 | 5 | 0 | 0 | 0 | 0 | 5 | 0 | 5 | 0 | 0 | 0 | 0 | 5 | 0 |
| 25 | 0.50 | PES | 10 | 10 | 0 | 10 | 10 | 0 | 10 | 0 | 5 | 5 | 5 | 0 | 0 | 0 | 20 | 0 | 30 | 0 | 0 |
|   | 1.00 | PES | 40 | 0 | 30 | 0 | 0 | 20 | 20 | 0 | 20 | 30 | 20 | 0 | 5 | 0 | 5 | 0 | 100 | 5 | 5 |
| 26 | 2.00 | PES | 100 | 10 | 5 | 5 | 5 | 5 | 10 | N | 90 | 5 | 30 | 0 | 5 | 0 | 0 | 5 | 10 | 5 | 0 |
| 30 | 2.00 | POS | 0 | 0 | 10 | 0 | 5 | 0 | 20 | 0 | 20 | 20 | 5 | 0 | 5 | 0 | 0 | 10 | 50 | 0 | 5 |
|   | 2.00 | PES | 100 | 5 | 0 | 0 | 5 | 0 | 20 | N | 90 | 20 | 5 | 0 | 25 | 5 | 0 | 0 | 10 | 5 | 0 |
|   | 2.00 | POS | 0 | 5 | 0 | 5 | 5 | 10 | 20 | 5 | 20 | 20 | 20 | 0 | 0 | 0 | 0 | 10 | 100 | 5 | 5 |
| 36 | 2.00 | PES | 100 | 0 | 0 | 0 | 0 | 0 | 40 | N | 100 | 90 | 5 | 0 | 0 | 0 | 20 | 0 | 20 | 0 | 5 |
|   | 2.00 | POS | 0 | 5 | 0 | 5 | 5 | 5 | 5 | 5 | 20 | 60 | 20 | 0 | 25 | 0 | 5 | 0 | 100 | 5 | 0 |
| 40 | 1.00 | PES | 95 | 80 | 70 | 40 | 40 | 80 | 100 | N | 40 | 10 | 5 | 0 | 0 | 0 | 20 | 0 | 100 | 10 | 10 |
| 45 | 0.25 | PES | 100 | 80 | 80 | 80 | 80 | 100 | 100 | 0 | 80 | 90 | 20 | 0 | 5 | 5 | 30 | 5 | 100 | 10 | 10 |
|   | 0.50 | PES | 100 | 85 | 90 | 80 | 85 | 80 | 100 | 5 | 80 | 100 | 30 | 0 | 20 | 10 | 70 | 10 | 100 | 20 | 40 |
|   | 1.00 | PES | 60 | 20 | 30 | 20 | 10 | 60 | 10 | 15 | 50 | 20 | 40 | 0 | 10 | 0 | 5 | 0 | 90 | 10 | 50 |
|   | 0.50 | POS | 100 | 30 | 50 | 30 | 30 | 80 | 25 | 0 | 60 | 30 | 20 | 0 | 20 | 0 | 10 | 10 | 100 | 10 | 60 |
| 47 | 0.25 | PES | 100 | 80 | 100 | 70 | 70 | 90 | 5 | 5 | 30 | 60 | 20 | 0 | 10 | 0 | 15 | 0 | 90 | 10 | 5 |
|   | 0.50 | PES | 70 | 10 | 30 | 20 | 10 | 80 | 5 | 5 | 50 | 90 | 30 | 0 | 5 | 5 | 20 | 5 | 100 | 15 | 5 |
|   | 1.00 | POS | 95 | 10 | 60 | 20 | 20 | 80 | 5 | 10 | 30 | 90 | 5 | 0 | 10 | 10 | 20 | 0 | 100 | 10 | 10 |
|   | 1.00 | PES | 100 | 30 | 80 | 20 | 30 | 100 | 20 | 0 | 90 | 100 | 10 | 0 | 10 | 0 | 40 | 10 | 100 | 15 | 10 |
| 48 | 0.25 | PES | 100 | 30 | 80 | 20 | 20 | 30 | 5 | 5 | 90 | 30 | 20 | 0 | 20 | 5 | 10 | 0 | 90 | 15 | 5 |
|   | 0.50 | POS | 0 | 0 | 0 | 0 | 0 | 0 | 0 | 0 | 0 | 0 | 5 | 0 | 0 | 0 | 5 | 0 | 50 | 5 | 5 |
|   | 1.00 | PES | 10 | 10 | 0 | 0 | 0 | 0 | 10 | 5 | 80 | 10 | 5 | 0 | 20 | 5 | 5 | 0 | 5 | 0 | 10 |
| 50 | 0.25 | PES | 10 | 10 | 10 | 10 | 10 | 10 | 10 | 0 | 85 | 90 | 5 | 0 | 30 | 0 | 60 | 40 | 100 | 30 | 5 |
|   | 0.50 | PES | 100 | 100 | 100 | 80 | 80 | 80 | 70 | 5 | 100 | 95 | 50 | 0 | 90 | 40 | 80 | 50 | 100 | 50 | 20 |
|   | 1.00 | POS | 100 | N | N | N | N | N | 75 | N | N | Z | 80 | Z | Z | N | Z | Z | Z | Z | N |
|   | 0.25 | PES | 100 | 30 | 50 | 30 | 30 | 80 | 80 | 5 | 100 | 100 | 20 | 0 | 60 | 10 | 10 | 0 | 100 | 10 | 60 |
|   | 0.06 | PES | 100 | 30 | 40 | 10 | 20 | 50 | 20 | N | 20 | 20 | 30 | 0 | 5 | 5 | 5 | 0 | 60 | 5 | 5 |
|   | 0.13 | PES | 100 | 80 | 70 | 40 | 50 | 60 | 20 | 30 | 60 | 30 | 30 | 0 | 10 | 5 | 10 | 0 | 95 | 5 | 10 |
|   | 0.25 | PES | 100 | 90 | 90 | 60 | 50 | 85 | 90 | 0 | 50 | 50 | 70 | 0 | 20 | 5 | 20 | 0 | 95 | 15 | 10 |
| 58 | 1.00 | PES | 10 | 10 | 5 | 0 | 10 | 10 | 20 | 0 | 60 | 30 | 40 | 0 | 5 | 10 | 40 | 5 | 50 | 15 | 5 |
|   | 1.00 | POS | 100 | 90 | 80 | 40 | 50 | 80 | 20 | 5 | 50 | 30 | 20 | 0 | 20 | 0 | 10 | 0 | 100 | 20 | 10 |
| 59 | 1.00 | PES | 10 | 0 | 5 | 0 | 0 | 5 | 30 | N | 60 | 30 | 30 | 0 | 5 | 0 | 30 | 5 | 50 | 5 | 5 |
| 60 | 1.00 | POS | 100 | 80 | 30 | 20 | 20 | 50 | 20 | N | 30 | 10 | 0 | 5 | 60 | 0 | 0 | 0 | 50 | 5 | 5 |
|   | 1.00 | PES | 5 | 0 | 0 | 0 | 0 | 0 | 5 | N | 10 | 5 | 5 | 0 | 5 | 0 | 5 | 0 | 10 | 5 | 0 |
| 61 | 1.00 | PES | 20 | 20 | 10 | 5 | 0 | 0 | 0 | N | 10 | 10 | 0 | 5 | 0 | 0 | 0 | 0 | 5 | 10 | 0 |
| 62 | 1.00 | PES | 10 | 10 | 5 | 0 | 0 | 0 | 5 | 0 | 0 | 5 | 0 | 0 | 5 | 0 | 0 | 0 | 5 | 0 | 0 |

N = Not tested.

Test No. 3

Greenhouse Test—Post-Emergence Post-Flood Application

This test illustrates the herbicidal activity of the various compounds listed below in the control of several broadleaf and grass weed species commonly associated with rice crops. The species tested were as follows:

| Common Name | Scientific Name | Abbreviation |
| --- | --- | --- |
| Broadleaf Weeds: | | |
| annual morningglory | Ipomoea purpurea | AMG |
| hemp sesbania | Sesbania exaltata | SESB |
| Grasses: | | |
| yellow nutsedge | Cyperus esculentus | YNS |
| watergrass | Echinochloa crusgalli | WG |

The effect of the compounds on a rice crop (RC) grown adjacent to the weeds is also observed. Simulations of flooded rice paddies were used for this test. The weed species and rice were planted simultaneously. Both direct seeded and transplanted rice were used to represent common growing techniques. The procedure was as follows:

Plastic tubs measuring 11.1 inches (28.2 cm) in depth, 6.7 inches (17.0 cm) in width, and 5.3 inches (13.5 cm) in depth were lined with plastic and filled to a depth of 2–3 inches (5.1–7.6 cm) with sandy loam soil containing 50 parts per million by weight (ppm) of cis-N-[(trichloromethyl)thio]-4-cyclohexene-1,2-dicarboximide (a commercial fungicide known as "Captan") and 17-17-17 (percentages of $N-P_2O_5-K_2O$ on a weight basis) fertilizer.

On the 15th day after planting, the soil in each tub was flooded under 2–3 inches (5.1–7.6 cm) of water. The watergrass was in the two-leaf stage by this time and was completely submerged by the water. The other weed species and the rice were all at the water line or slightly above. The test compounds were then added on the next day to the flood water from stock solutions made by dissolving 88 mg of test compound in 40 ml acetone containing 0.1% (by weight) of a polyoxyethylene sorbitan monolaurate surface-active agent. Aliquots of the appropriate amount of solution were used to provide an application rate ranging from 0.13 to 2.0 pounds of active ingredient per acre (0.14 to 2.24 kilograms per hectare) in equivalent terms.

The water level was then maintained in each tub for three weeks, at which time each species was evaluated for percent injury. The evaluation was a visual rating comparing the treated plants to untreated plants grown under otherwise identical conditions in a separate tub. The ratings ranged from 0 to 100%, with 0 representing no injury and 100% representing complete kill. The injury ratings represented total plant injury due to all factors. The results are shown in Table IV.

TABLE IV

| Compound No. | Application rate (lb/A) | Rice Screen - Post-Flood Application Percent Injury | | | | |
| --- | --- | --- | --- | --- | --- | --- |
| | | WG | AMG | SESB | YNS | RC |
| 2 | 1.00 | 65 | 55 | 95 | 20 | 10 |
|  | 2.00 | 70 | 65 | 90 | 45 | 35 |
| 17 | 1.00 | 75 | 0 | 30 | 25 | 20 |
|  | 2.00 | 75 | 0 | 35 | 30 | 40 |
| 25 | 1.00 | 60 | 80 | 20 | 0 | 20 |
|  | 2.00 | 75 | 100 | 40 | 0 | 20 |
| 45 | 0.25 | 80 | 80 | 40 | 0 | 30 |
|  | 0.50 | 80 | 60 | 40 | 0 | 60 |
|  | 1.00 | 85 | 100 | 100 | 0 | 65 |
|  | 1.00 | 100 | 100 | 40 | 30 | 50 |
|  | 2.00 | 100 | 100 | 100 | 30 | 75 |
|  | 1.00 | N | N | N | N | N |
|  | 1.00 | N | N | N | N | N |
| 50 | 0.25 | 60 | 30 | 20 | 0 | 50 |
|  | 0.50 | 75 | 30 | 50 | 0 | 70 |
|  | 1.00 | 80 | 50 | 40 | 0 | 85 |
|  | 0.13 | 80 | 100 | 100 | 0 | 0 |
|  | 0.25 | 100 | 100 | 100 | 0 | 20 |
|  | 0.50 | 100 | 100 | 100 | 0 | 35 |
|  | 0.13 | 100 | 30 | 8 | 0 | 10 |
|  | 0.25 | 100 | 100 | 90 | 0 | 50 |
|  | 0.50 | 100 | 100 | 100 | 0 | 55 |
|  | 1.00 | 100 | 100 | 100 | 0 | 85 |
|  | 1.00 | 95 | 100 | 95 | 20 | 50 |
|  | 2.00 | 80 | 100 | 80 | 25 | 80 |
|  | 1.00 | 100 | 100 | 100 | 0 | 95 |
|  | 1.00 | 100 | 100 | 100 | 0 | 25 |
| 58 | 0.13 | 0 | 15 | 25 | 0 | 0 |
|  | 0.25 | 30 | 25 | 75 | 0 | 15 |
|  | 0.50 | 40 | 100 | 80 | 0 | 10 |
|  | 0.13 | 0 | 0 | 0 | 0 | 0 |
|  | 0.25 | 40 | 20 | 0 | 0 | 10 |
|  | 0.50 | 65 | 30 | 20 | 0 | 10 |
|  | 1.00 | 100 | 50 | 70 | 0 | 25 |
|  | 1.00 | 70 | 80 | 0 | 0 | 35 |
|  | 2.00 | 80 | 100 | 50 | 0 | 35 |

Test No. 4

Still another series of tests were conducted against a series of weed species commonly found in Europe. These weed species were as follows:

| Common Name | Scientific Name | Abbreviation |
| --- | --- | --- |
| blackgrass | Alopecurus myosuroides | BKGR |
| perennial ryegrass | Lolium perrenne | PRGR |
| wild oat | Avena fatua | WO |
| poverty brome | Bromus sterilis | PBRO |
| scented mayweed | Matricaria recutita | MARE |
| common chickweed | Stellaria media | CCHW |
| ivyleaf seedwell | Veronica hederifolis | ILSW |
| mustard | Sinapis arvensis | MD |
| carrot | Daucus catora | CARO |
| catchweed bedstraw | Galium aparine | BDSW |

Also included in this series of tests were various crop species as follows:

| | | |
| --- | --- | --- |
| sugarbeet - Amazon | Beta vulgaris | SB |
| barley | Hordeum vulgare | BA |
| wheat | Triticum aestivum | WH |

Aluminum loaf pans measuring 19×8×6 cm were filled with loamy sand soil amended with 75 ppm Captan fungicide. Six furrows were made across the width of the pan. Seeds were placed in the furrows and then covered with soil. Some species, namely Matricaria recutita and Stellaria media were sown on the soil surface to ensure adequate germination and establishment. Two loaf pans were used for each treatment for a total of 12 plant species. Three of the 12 plant species were crops: sugarbeets, winter barley and winter wheat. Remaining species were monocot and dicot weeds associated with those crops.

Flats to be treated with a pre-emergence spray treatment were immediately treated after seeding, and before watering of the flats. Flats to be treated with a post-emergence spray treatment were kept in the greenhouse and grown until ready for treatment. Dicots had the first true leaf tissue expanded, and monocots had one to two leaves at the time of treatment.

Chemicals were weighed into 60 ml clear bottles using a Sartorius scale. The amount of chemical needed was determined from the following information:

ronment helps to simulate the field environment in which these crops and weeds grow.

Three to four weeks after treatment, each row of seedlings or plants was visually rated for growth, injury or control due to all facts of herbicide or chemical affect. Symptomologies were recorded for each compound showing activity. Untreated flats were used for comparison, and their growth was considered as 0% injury. One hundred percent injury was equivalent to complete kill.

The results are shown in Table V.

TABLE V

| Cmpd. No. | Application Rate (lb/A) | Method | BKGR | PRGR | WO | PBRO | MARE | CCHW | BDSW | ILSW | MD | SB | BA | WH | CARO |
|---|---|---|---|---|---|---|---|---|---|---|---|---|---|---|---|
| 25 | 2.00 | PES | 20 | 20 | 0 | 0 | 30 | 50 | 20 | 0 | 90 | 40 | 0 | 0 | N |
| 30 | 2.00 | POS | 20 | 0 | 0 | 0 | 0 | 40 | 30 | N | 100 | 100 | 0 | 0 | N |
| 36 | 2.00 | PES | 0 | 0 | 10 | 0 | 0 | 0 | 20 | N | 0 | 0 | 0 | 0 | 0 |
|  | 2.00 | POS | 20 | 0 | 40 | 0 | 20 | 40 | 40 | N | 95 | 100 | 0 | 0 | 0 |
| 40 | 2.00 | PES | 15 | 0 | 0 | 10 | 0 | 0 | 0 | N | 70 | 50 | 0 | 0 | 0 |
| 45 | 2.00 | PES | 100 | 75 | 60 | N | 80 | 90 | 50 | N | 65 | 90 | 45 | 30 | 30 |
|  | 2.00 | POS | 45 | 60 | 80 | N | 20 | 40 | 45 | N | 95 | 90 | 60 | 45 | 75 |
| 47 | 2.00 | PES | 95 | 50 | 60 | N | 50 | 20 | 40 | N | 55 | 100 | 20 | 10 | 0 |
| 50 | 2.00 | PES | 100 | 100 | 100 | N | 85 | 100 | 60 | N | 95 | 100 | 90 | 95 | 100 |
|  | 2.00 | POS | 65 | 95 | 80 | N | 45 | 95 | 65 | N | 90 | 100 | 75 | 75 | 85 |
|  | 0.25 | PES | 100 | 100 | 50 | N | 70 | 75 | 35 | N | 70 | 100 | 65 | 50 | 0 |
|  | 0.50 | PES | 100 | 100 | 90 | N | 75 | 95 | 45 | N | 80 | 100 | 70 | 70 | 15 |
|  | 1.00 | PES | 100 | 100 | 95 | N | 100 | 100 | 55 | N | 95 | 100 | 85 | 85 | 20 |
|  | 2.00 | PES | 100 | 100 | 100 | N | 100 | 100 | 65 | N | 100 | 100 | 90 | 95 | 45 |
| 58 | 2.00 | PES | 100 | 95 | 70 | N | 50 | 60 | 25 | N | 20 | 100 | 20 | 10 | 0 |
|  | 2.00 | POS | 40 | 40 | 30 | N | 20 | 90 | 40 | N | 70 | 100 | 25 | 20 | 0 |
|  | 0.25 | PES | 70 | 60 | 30 | N | 20 | 0 | 20 | N | 20 | 20 | 0 | 0 | N |
|  | 0.50 | PES | 95 | 65 | 55 | N | 30 | 20 | 30 | N | 30 | 35 | 20 | 30 | N |
|  | 1.00 | PES | 100 | 90 | 60 | N | 30 | 25 | 35 | N | 45 | 45 | 25 | 30 | N |
|  | 2.00 | PES | 100 | 95 | 70 | N | 30 | 45 | 40 | N | 50 | 95 | 30 | 55 | N |
| 59 | 2.00 | PES | 50 | 40 | 30 | N | 25 | 30 | 15 | 0 | 20 | 20 | 0 | 0 | 0 |
|  | 2.00 | POS | 40 | 30 | 30 | N | 40 | 95 | 30 | 0 | 90 | 100 | 20 | 15 | 0 |
| 61 | 2.00 | PES | 10 | 0 | 0 | N | 15 | 20 | 15 | 0 | 10 | 40 | 0 | 0 | 0 |
| 62 | 2.00 | PES | 15 | 10 | 0 | N | 0 | 15 | 0 | 0 | 0 | 30 | 0 | 0 | 0 |

| Carrier Volume (gallons/acre) | mg Chemical/ml Solvent |
|---|---|
| 20 | 6.0 = 1.0 pound active ingredient/acre |
| 25 | 4.8 = 1.0 pound active ingredient/acre |
| 30 | 4.0 = 1.0 pound active ingredient/acre |
| 40 | 3.0 = 1.0 pound active ingredient/acre |
| 50 | 2.4 = 1.0 pound active ingredient/acre |
| 80 | 1.5 = 1.0 pound active ingredient/acre |

Forty gallons/acre was the carrier volume used unless otherwise stated.

A 1:1 ratio of acetone/water was used to solve technical grade compounds to form a spray solution. Polyoxyethylene sorbitan monlaurate (Tween ®20) was added to the acetone at a concentration of 1%. The chemicals were first solved in this mixture before addition of the water. The total solution volume for each treatment was 40 ml. Only water was used to put formulated materials into solution.

Spray solutions were delivered to the soil surface or foliage by use of a linear spray table operated at 30 PSI. Flats were immediately placed in the greenhouse after spraying. Pre-emergence treated flats were watered from overhead. Foliage of post-emergence treatments was not dosed with water so as to maintain placement of the chemical.

Greenhouse air temperatures ranged from 15° C. to 24° C. during the year. Whitewash was maintained on the glazing all year in order to reduce light intensities as much as possible. A cool and shady greenhouse envi- The N,N'-diaryl-N-alkylureas of this invention can also be utilized as intermediates for the preparation of certain 2-iminophenylthiazolidine compounds which are also herbicides. These compounds are described in co-pending application Ser. No. 123,133, filed Nov. 27, 1987, and can be made when the N,N'-diaryl-N-alkylureas of this invention have an $R_5$ substituent which is an alkenyl, a hydroxyalkyl, or a haloalkyl moiety.

In those instances, the N,N'-diaryl-N-alkylureas are treated with hydrogen or halogen ion sources such as sulfuryl chloride or other suitable chloronium sources to produce the aforementioned thiazolidine compounds. This process can be illustrated as follows wherein the $R_5$ constituent is an alkenyl moiety.

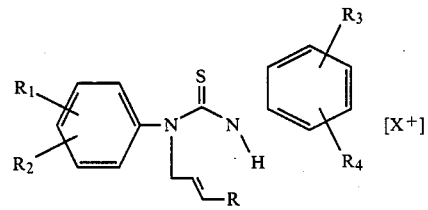

-continued

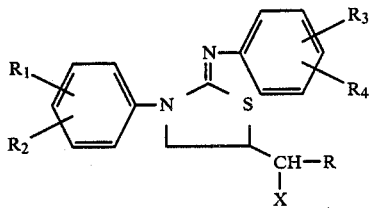

The reaction is conducted at ambient temperatures, normally room temperatures. The hydrogen or halogen ion source [X+] set forth is preferably sulfuryl chloride, but other ion sources, such as hydrochloric acid, trifluoromethanesulfonic acid and the like can be used.

Example 11 below illustrates the preparation of one such thiazolidine compound.

EXAMPLE 11

Preparation of 2-(4-Chloro)phenylimino-3-(3-trifluoromethyl)phenyl-5-chloromethylthiazolidine Two grams (5.39 mmole) of N-allyl-N-(3-trifluoromethyl)phenyl-N'-3-chlorophenyl thiourea in 50 ml of dry (passed over alumina) $CH_2Cl_2$ was added to a 100 ml round-bottomed flask equipped with a magnetic stirrer. The flask was then placed in a water bath at 20° C. and the contents stirred. A solution of 0.73 g (5.41 mmol) of $SO_2Cl_2$ in 10 ml of dry $CH_2Cl_2$ was then added dropwise over 5 minutes and when the addition was complete the stirring was continued for an additional 7 hours. The solution was then washed with two 50 ml portions of saturated $K_2CO_3$, dried ($Na_2SO_4$) and the solvent removed in vacuo. Chromatography of the residual oil on silica gel with 2:1 hexanes/$CH_2Cl_2$ as eluent afforded 2.10 g (96%) of the subject compound, identified as such by suitable analytical techniques.

Other thiazolidine compounds of the type described in application Ser. No. 126,133, filed Nov. 27, 1987 can be made in a similar manner.

METHODS OF APPLICATION

The herbicidal compositions of the present invention are useful in controlling the growth of undesirable vegetation by pre-emergence or post-emergence application to the locus where control is desired, including pre-plant and post-plant soil incoporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very freeflowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural useage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Post-emergent application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. An N,N'-diaryl-N-alkylurea having the formula

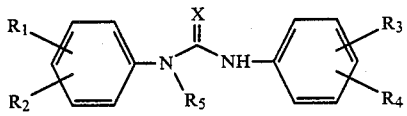

wherein $R_1$, $R_2$, $R_3$ and $R_4$ are the same or different and are selected from the group consisting of hydrogen, halogen, cyano, trifluoromethyl, trifluoromethylthio, trifluoromethyl thionyl, trifluoromethane sulfonyl, sulfonamido, substituted phenoxy and substituted pyridyloxy groups wherein the substituent is any one of halogen, cyano, trifluoromethyl, trifluoromethylthio, trifluoromethyl thionyl, trifluoromethane sulfonyl, sulfonamido; and $R_5$ is selected from the group consisting of alkyl, alkenyl, haloalkyl, haloalkenyl, hydroxyalkyl, hydroxylalkenyl, acetoxyalkyl, acetoxyalkenyl, mercaptoalkyl, and mercaptoalkenyl, wherein the alkyl or alkenyl group in each alkyl- or alkenyl-containing moiety has from 3 to 6 carbon atoms; and X is oxygen or sulfur.

2. The compound of claim 1 wherein $R_1$ is hydrogen, $R_2$ is 3-trifluoromethyl, $R_3$ is hydrogen, $R_4$ is 4-cyano, $R_5$ is $CH_2CH=CH_2$ and X is sulfur.

3. The compound of claim 1 wherein $R_1$ is hydrogen, $R_2$ is 3-trifluoromethyl, $R_3$ is hydrogen, $R_4$ is 4-cyano, $R_5$ is $CH_2CHClCH_2CH_3$ and X is oxygen.

4. The compound of claim 1 wherein $R_1$ is hydrogen, $R_2$ is 3-trifluoromethyl, $R_3$ is hydrogen, $R_4$ is 4-fluoro, $R_5$ is $CH_2CHClCH_2CH_3$ and X is oxygen.

5. The compound of claim 1 wherein $R_1$ is hydrogen, $R_2$ is 3-trifluoromethyl, $R_3$ is hydrogen, $R_4$ is 3-nitro, $R_5$ is $CH_2CHClCH_2CH_3$ and X is oxygen.

6. The compound of claim 1 wherein $R_1$ is hydrogen, $R_2$ is 3-trifluoromethyl, $R_3$ is hydrogen, $R_4$ is 3-fluoro, $R_5$ is $CH_2CHClCH_2CH_3$ and X is oxygen.

7. A herbicidal composition which comprises an herbicidally effective amount of an N,N'-diaryl-N-alkylurea having the formula

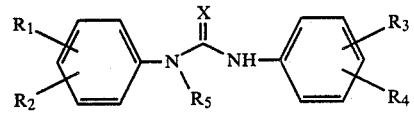

wherein $R_1$, $R_2$, $R_3$ and $R_4$ are the same or different and are selected from the group consisting of hydrogen, halogen, cyano, trifluoromethyl, trifluoromethylthio, trifluoromethyl thionyl, trifluoromethane sulfonyl, sulfonamido, substituted phenoxy and substituted pyridyloxy groups wherein the substituent is any one of halogen, cyano, trifluoromethyl, trifluoromethylthio, trifluoromethyl thionyl, trifluoromethane sulfonyl, sulfonamido; and $R_5$ is selected from the group consisting of alkyl, alkenyl, haloakyl, haloakenyl, hydroxyalkyl, hydroxylalkenyl, acetoxyalkyl, acetoxyalkenyl, mercaptoalkyl, and mercaptoalkenyl, wherein the alkyl or alkenyl group in each alkyl- or alkenyl-containing moiety has from 3 to 6 carbon atoms; and X is oxygen or sulfur; and an inert diluent carrier therefor.

8. The composition of claim 7 wherein $R_1$ is hydrogen, $R_2$ is 3-trifluoromethyl, $R_3$ is hydrogen, $R_4$ is 4-cyano, $R_5$ is $CH_2CH=CH_2$ and X is sulfur.

9. The composition of claim 7 wherein $R_1$ is hydrogen, $R_2$ is 3-trifluoromethyl, $R_3$ is hydrogen, $R_4$ is 4-cyano, $R_5$ is $CH_2CHClCH_2CH_3$ and X is oxygen.

10. The composition of claim 7 wherein $R_1$ is hydrogen, $R_2$ is 3-trifluoromethyl, $R_3$ is hydrogen, $R_4$ is 4-fluoro, $R_5$ is $CH_2CHClCH_2CH_3$ and X is oxygen.

11. The composition of claim 7 wherein $R_1$ is hydrogen, $R_2$ is 3-trifluoromethyl, $R_3$ is hydrogen, $R_4$ is 3-nitro, $R_5$ is $CH_2CHClCH_2CH_3$ and X is oxygen.

12. The composition of claim 7 wherein $R_1$ is hydrogen, $R_2$ is 3-trifluoromethyl, $R_3$ is hydrogen, $R_4$ is 3-fluoro, $R_5$ is $CH_2CHClCH_2CH_3$ and X is oxygen.

13. A method for controlling undesirable weed pests which comprises applying to the locus where control is desired an herbicidally effective amount of an N,N'-diaryl-N-alkylurea having the formula

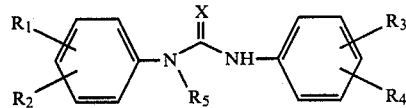

wherein $R_1$, $R_2$, $R_3$ and $R_4$ are the same or different and are selected from the group consisting of hydrogen, halogen, cyano, trifluoromethyl, trifluoromethylthio, trifluoromethyl thionyl, trifluoromethane sulfonyl, sulfonamido, substituted phenoxy and substituted pyridyloxy groups wherein the substituent is any one of halogen, cyano, trifluoromethyl, trifluoromethylthio, trifluoromethyl thionyl, trifluoromethane sulfonyl, sulfonamido; and $R_5$ is selected from the group consisting of alkyl, alkenyl, haloalkyl, haloalkenyl, hydroxyalkyl, hydroxylalkenyl, acetoxyalkyl, acetoxyalkenyl, mercaptoalkyl, and mercaptoalkenyl, wherein the alkyl or alkenyl group in each alkyl- or alkenyl-containing moiety has from 3 to 6 carbon atoms; and X is oxygen or sulfur.

14. The method of claim 13 wherein $R_1$ is hydrogen, $R_2$ is 3-trifluoromethyl, $R_3$ is hydrogen, $R_4$ is 4-cyano, $R_5$ is $CH_2CH=CH_2$ and X is sulfur.

15. The method of claim 13 wherein $R_1$ is hydrogen, $R_2$ is 3-trifluoromethyl, $R_3$ is hydrogen, $R_4$ is 4-cyano, $R_5$ is $CH_2CHClCH_2CH_3$ and X is oxygen.

16. The method of claim 13 wherein $R_1$ is hydrogen, $R_2$ is 3-trifluoromethyl, $R_3$ is hydrogen, $R_4$ is 4-fluoro, $R_5$ is $CH_2CHClCH_2CH_3$ and X is oxygen.

17. The method of claim 13 wherein $R_1$ is hydrogen, $R_2$ is 3-trifluoromethyl, $R_3$ is hydrogen, $R_4$ is 3-nitro, $R_5$ is $CH_2CHClCH_2CH_3$ and X is oxygen.

18. The method of claim 13 wherein $R_1$ is hydrogen, $R_2$ is 3-trifluoromethyl, $R_3$ is hydrogen, $R_4$ is 3-fluoro, $R_5$ is $CH_2CHClCH_2CH_3$ and X is oxygen.

* * * * *